(12) United States Patent
Prien et al.

(10) Patent No.: US 6,615,592 B2
(45) Date of Patent: Sep. 9, 2003

(54) METHOD AND SYSTEM FOR PREPARING TISSUE SAMPLES FOR HISTOLOGICAL AND PATHOLOGICAL EXAMINATION

(75) Inventors: Samuel D. Prien, Shallowater, TX (US); John Blanton, Lubbock, TX (US); Brian Wood, Lubbock, TX (US); Allan J. Cassell, West Heidelberg (AU)

(73) Assignee: Supachill Technologies Pty. Ltd., West Heidelberg (AU)

(*) Notice: Subject to any disclaimer, the term of this patent is extended or adjusted under 35 U.S.C. 154(b) by 0 days.

(21) Appl. No.: 10/034,999

(22) Filed: Dec. 28, 2001

(65) Prior Publication Data

US 2002/0100284 A1 Aug. 1, 2002

Related U.S. Application Data

(60) Provisional application No. 60/259,418, filed on Jan. 2, 2001.

(51) Int. Cl.$^7$ .......................... F25D 17/02; F25B 19/00; C12N 5/00
(52) U.S. Cl. ..................... 62/64; 62/376; 62/51.1; 435/374
(58) Field of Search ..................... 62/64, 373, 375, 62/376, 62, 51.1; 435/374, 1.3

(56) References Cited

U.S. PATENT DOCUMENTS

| | | | |
|---|---|---|---|
| 3,412,476 A | 11/1968 | Astrom | 34/147 |
| 3,653,494 A | 4/1972 | Miller | 198/195 |
| 3,866,432 A | 2/1975 | Harrison | 62/208 |

(List continued on next page.)

FOREIGN PATENT DOCUMENTS

| | | | |
|---|---|---|---|
| AU | 2120099 | 9/1999 | F25D/17/02 |
| DE | 1238618 | 4/1967 | |
| EP | 0 174 170 A2 | 8/1985 | F25D/17/02 |

(List continued on next page.)

OTHER PUBLICATIONS

Database–BIOSIS Online!, Biosciences Information Service, Philadelphia, PA, US; R.P. Cohen et al.: "Predicting Cold Tolerance In Perennial Ryegrass Lolium–Perenne Through Alcohol Bath Freezing of Seedling Plants"; XP002187229 abstract & Agronomy Journal, vol. 30, 1986, pp. 560–563.

*Primary Examiner*—William C. Doerrler
(74) *Attorney, Agent, or Firm*—Raymond M. Galasso; Simon, Galasso & Frantz PLC

(57) ABSTRACT

Viable biological material is cryogenically preserved (cryopreservation) by immersing the material in a tank of cooling fluid, and circulating the cooling fluid past the material at a substantially constant predetermined velocity and temperature to freeze the material. The material may either be directly plunged into the cooling fluid without preparation, or chemically prepared prior to freezing. A method according to the present invention freezes the biologic material quickly enough to avoid the formation of ice crystals within cell structures (vitrification) and allows the samples to maintain anatomical structure and remain biochemically active after thaw. The temperature of the cooling fluid is preferably between –20 degrees centigrade and –30 degrees centigrade, which is warm enough to minimize the formation of stress fractures and other artefacts in cell membranes due to thermal changes. Cells frozen using a method according to the present invention have been shown to have a significantly less cellular and intercellular damage than cells frozen by other cryopreservation methods used for pathological and histological techniques. Because the present invention can freeze biological material such that the material is vitrified, biochemical activity within the cell is not lost after freezing and thus various embodiments of the present method may be employed in a system to prepare biological material for the newer techniques of cryopathology and immunohistochemistry in the areas of research and patient care.

39 Claims, 5 Drawing Sheets

U.S. PATENT DOCUMENTS

| | | | |
|---|---|---|---|
| 4,167,101 A | 9/1979 | Rojey | 62/102 |
| 4,311,019 A | 1/1982 | Rojey et al. | 62/101 |
| 4,429,542 A | 2/1984 | Sakao et al. | 62/62 |
| 4,480,445 A | 11/1984 | Goldstein | 62/123 |
| 4,554,797 A | 11/1985 | Goldstein | 62/434 |
| 4,619,257 A * | 10/1986 | Linner et al. | 606/20 |
| 4,647,543 A * | 3/1987 | Stocker | 436/174 |
| 4,676,070 A | 6/1987 | Linner | 62/64 |
| 4,848,094 A | 7/1989 | Davis et al. | 62/64 |
| 4,888,956 A * | 12/1989 | le Roux Murray | 62/51.1 |
| 4,901,844 A | 2/1990 | Palmaer et al. | 198/778 |
| 4,971,842 A | 11/1990 | Sippola | 427/433 |
| 4,985,169 A | 1/1991 | Rolland et al. | 252/69 |
| 5,003,787 A | 4/1991 | Zlobinsky | 62/185 |
| 5,022,236 A * | 6/1991 | Knippscheer et al. | 62/529 |
| 5,191,773 A | 3/1993 | Cassell | 62/373 |
| 5,222,367 A | 6/1993 | Yamada | 62/64 |
| 5,328,821 A * | 7/1994 | Fisher et al. | 435/1.3 |
| 5,496,456 A | 3/1996 | Fischer et al. | 204/201 |
| 5,560,956 A * | 10/1996 | Schmehl | 427/2.11 |
| 5,638,686 A * | 6/1997 | Coelho et al. | 62/51.1 |
| 5,860,282 A | 1/1999 | Liberman et al. | 62/63 |
| 5,873,254 A * | 2/1999 | Arav | 62/63 |
| 5,891,617 A * | 4/1999 | Watson et al. | 435/1.3 |
| 6,140,123 A * | 10/2000 | Demetriou et al. | 435/374 |

FOREIGN PATENT DOCUMENTS

| | | | | |
|---|---|---|---|---|
| EP | 0 275 114 A2 | 7/1988 | | F25C/1/00 |
| EP | 0 331 296 A1 | 9/1989 | | A23B/7/144 |
| GB | 765760 | 1/1957 | | |
| GB | 999377 | 7/1965 | | |
| GB | 1 395 651 | 5/1975 | | A61J/3/02 |
| GB | 2 146 418 A | 4/1985 | | F25D/3/00 |
| JP | 63 273776 | 11/1988 | | F25D/13/06 |
| JP | 64000219 | 1/1989 | | C21D/1/18 |
| JP | 02126075 | 5/1990 | | F25D/13/00 |
| WO | WO 91/02202 | 2/1991 | | F25D/23/02 |
| WO | WO 97/35155 | 9/1997 | | F25D/31/00 |
| WO | WO 01/95716 A2 | 12/2001 | | A01N/1/00 |

* cited by examiner

METHOD AND SYSTEM FOR PREPARING TISSUE SAMPLES FOR HISTOLOGICAL AND PATHOLOGICAL EXAMINATION

CROSS REFERENCE TO RELATED APPLICATION

This application claims benefit under 35 U.S.C. §119 of the following U.S. provisional patent application Serial No. 60/259,418, entitled "Method And System For Preparing Tissue Samples For Histological And Pathological Examination", which was filed on Jan. 2, 2001.

FIELD OF THE INVENTION

The present invention relates generally to cryogenic preservation and more particularly to a method of preserving for examination and diagnostic purposes.

BACKGROUND OF THE INVENTION

Biological materials such as tissues are subjected to various treatments in an histology laboratory to prepare specimens on slides for viewing under a microscope. Pathologists carefully examine the slides and report their findings, which aids physicians in the diagnosis of disease or disease processes. Histopathology has traditionally relied upon examination of samples prepared by one of two basic methods. In the first histological method, samples undergo significant processing in the laboratory, such as fixation to preserve tissues, dehydration to remove water from tissues, infiltration with embedding agents such as paraffin, embedment, sectioning or cutting sections of the tissue for placement on a slide, mounting the sections, and staining the sections to enhance details. The second method, cryogenic preparation, significantly reduces the processing of the first method in that it generally involves snap freezing in a cold liquid or environment, sectioning, mounting, and staining.

While the first method yields significantly superior visualization, it requires an extended period of time for processing, generally a minimum of 18 to 24 hours. Thus this method cannot be applied in situations where a rapid diagnosis of a pathologic process is required, such as during a surgical procedure. Additionally, the processing techniques employed may destroy all or part of the biological activity of the tissues.

The second method has the advantage of speed (30 minutes to 1 hour), however tissue specimens prepared using cryogenic preparation are often subject to cellular damage due to ice crystal formation, which can also cause the loss of biological function of molecules of interest within the tissues, and overall loss of tissue integrity manifested as degraded anatomical structure. Many commercial pathology laboratories discourage the use of frozen tissue for immunohistochemistry in all but special circumstances, because ice crystal formation in stored tissue causes many abnormal artifacts within the sample which make diagnostic interpretation quite difficult, or even impossible in some cases.

With the advent of poly- and then monoclonal antibodies, the focus of both traditional microscopic histology and pathology has shifted from simple subjective observation, to direct objective staining procedures. These newer immunohistochemistry (IHC) techniques help in determining diagnosis when histopathology alone proves inconclusive. However, IHC techniques are dependent on biologically intact receptors within the specimen for proper staining to occur. Therefore it is desirable to utilize a method of tissue specimen preparation that does not limit the amount of active biological material present after preparation is complete.

SUMMARY OF THE INVENTION

Therefore, what is needed is an improved way to cryogenically preserve viable single cells, tissues, organs, nucleic acids, or other biologically active molecules, that avoids at least some of the problems inherent in currently available methods. Accordingly, the present invention provides a method of cryopreservation for freezing a biochemically active tissue sample by immersing the sample in cooling fluid and circulating the cooling fluid past the material. The cooling fluid is circulated past the tissue sample at a substantially constant, predetermined velocity and temperature to freeze the tissue sample such that it is vitrified, yet the tissue sample maintains its anatomical structure and remains biochemically active after thaw. In at least one embodiment, the cooling fluid is maintained at a temperature of between about −20 degrees centigrade and −30 degrees centigrade, and the velocity of the cooling fluid past the tissue sample is about 35 liters per minute per foot of cooling fluid through an area not greater than about 24 inches wide and 48 inches deep. Additionally, at least one embodiment of the present invention immerses a biologically active tissue sample in cooling fluid to freeze the sample directly to a temperature higher than about −30 degrees centigrade. A further embodiment of the present invention provides for circulating the cooling fluid past a multi-path heat exchanging coil submersed in the cooling fluid, where the heat exchanging coil is capable of removing at least the same amount of heat from the cooling fluid as the cooling fluid removes from the tissue sample. At least one embodiment provides a system for implementing the above mentioned methods.

An object of at least one embodiment of the present invention is application of a method to freeze biological material wherein the formation of ice crystals and stress fractures is avoided, and cellular biochemical function is maintained after freezing.

An advantage of at least one embodiment of the present invention is that cryopreservation recovery rates are significantly increased, because biological material is vitrified during freezing.

Another advantage of at least one embodiment of the present invention is that cryopreservation recovery rates are improved, because biological material is vitrified at a high enough temperature to avoid the formation of stress fractures within cell membranes.

Another advantage of at least one embodiment of the present invention is that cryopreservation recovery rates are such that a considerably higher percentage of the biological material maintains its anatomical structure and remains biochemically active after thaw as compared to currently available methods.

An additional advantage of at least one embodiment of the present invention is that cryopreservation recovery rates are such that the biological material samples lend themselves to the application of sectioning, processing and subsequent histological, ultrastructural, and immunohistochemistry examination in shorter periods of time than traditional pathology techniques, thus shortening time to results.

A further advantage of at least one embodiment of the present invention is that once frozen, existing cryopreservation storage facilities and mechanisms can be used to store the frozen biological materials.

BRIEF DESCRIPTION OF THE DRAWINGS

Other objects, advantages, features and characteristics of the present invention, as well as methods, operation and functions of related elements of structure, and the combination of parts and economies of manufacture, will become apparent upon consideration of the following description and claims with reference to the accompanying drawings, all of which form a part of this specification, wherein like reference numerals designate corresponding parts in the various figures, and wherein:

DETAILED DESCRIPTION OF A PREFERRED EMBODIMENT OF THE INVENTION

In the following detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that logical, mechanical, chemical and electrical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
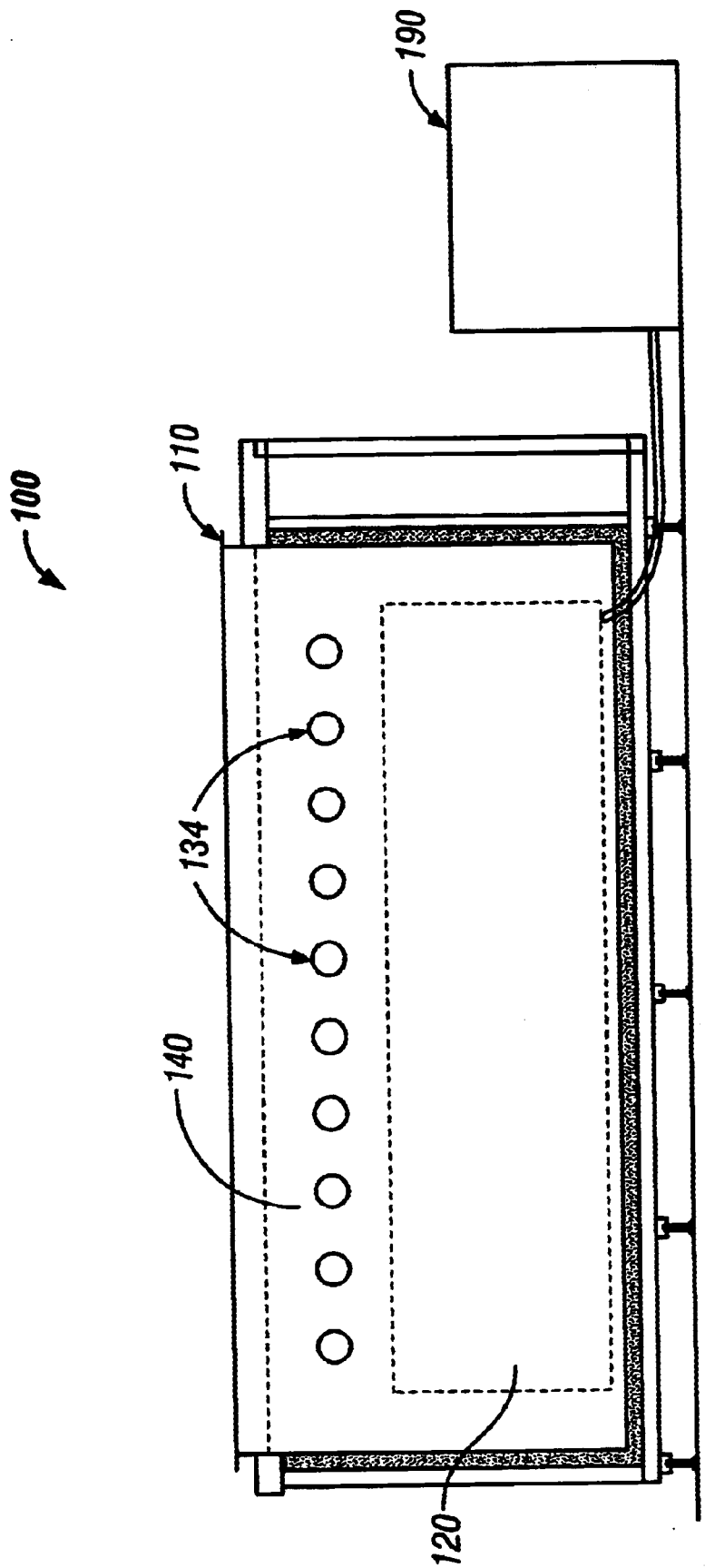
FIG. 1 is a side view of a chilling apparatus for practicing a method according to at least one embodiment of the present invention.
Figure 2:
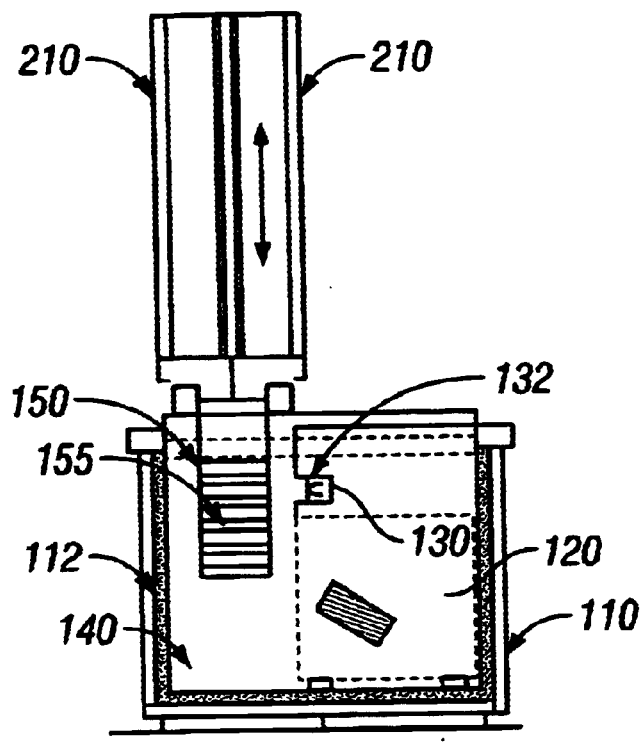
FIG. 2 is a cross sectional view of the chilling apparatus illustrated in FIG. 1 indicating implementation of cooling systems suitable for freezing relatively large quantities of biological material.

Referring first to FIGS. 1 and 2, a chilling apparatus suitable for practicing a method according to at least one embodiment of the present invention is discussed, and designated generally as cooling unit 100. Cooling unit 100 preferably comprises tank 110 containing cooling fluid 140. Submersed in cooling fluid 140 are circulators 134 such as motors 130 having impellers 132, heat exchanging coil 120, and rack 150, which in one embodiment comprises trays 155 for supporting biological material to be frozen. Biological material may include, but is not limited to, viable single cells, tissues and organs, nucleic acids, and other biologically active molecules. Biological material is not required to be species-specific. External to tank 110, and coupled to heat exchanging coil 120, is refrigeration unit 190.

Tank 110 may be of any dimensions necessary to immerse biological material to be frozen in a volume of cooling fluid 140, in which dimensions are scaled multiples of 12 inches by 24 inches by 48 inches. Other tank sizes may be employed consistent with the teachings set forth herein. For example, in one embodiment (not illustrated), tank 110 is sized to hold just enough cooling fluid 140, so containers such as vials, test tubes, beakers, graduated cylinders or the like, can be placed in tank 110 for rapid freezing of suspensions including biological materials and cryoprotectants. In other embodiments, tank 110 is large enough to completely immerse entire organs and or organisms for rapid freezing. It will be appreciated that tank 110 can be made larger or smaller as needed to efficiently accommodate various sizes and quantities of biological material to be frozen. The biological material may be treated with a cryoprotectant prior to being immersed in tank 110.

Tank 110 holds cooling fluid 140. In one embodiment, the cooling fluid is a food-grade solute. Good examples of food-grade quality fluids are those based on propylene glycol, sodium chloride solutions, or the like. In another embodiment, the cooling fluid is itself a cryoprotectant such as dimethylsulfoxide (DMSO), ethylene glycol, propylene glycol, polyethylene glycol or the like. Note that in some instances, the cryoprotectant is itself a food-grade quality fluid. In other embodiments, other fluids, and preferably solutes, are used as cooling fluids. While various containers may be used to hold the biological material, some embodiments of the present invention provide for the biological material to be directly immersed in the cooling fluid for rapid and effective freezing. Such direct immersion may simplify the cryopreservation of some tissues and organs.

In order to freeze biological material while avoiding the formation of ice crystals, one embodiment of the present invention circulates cooling fluid 140 past the biological material to be frozen, at a relatively constant rate of 35 liters per minute for every foot of cooling fluid contained in an area not more than about 24 inches wide by 48 inches deep. The necessary circulation is provided by one or more circulators 134, such as motors 130. In at least one embodiment of the present invention, submersed motors 130 drive impellers 132 to circulate cooling fluid 140 past biological material be to frozen. Other circulators 134, including various pumps (not illustrated), can be employed consistent with the objects of the present invention. At least one embodiment of the present invention increases the area and volume through which cooling fluid is circulated by employing at least one circulator 134, in addition to motors 130. In embodiments using multiple circulators 134, the area and volume of cooling fluid circulation are increased in direct proportion to each additional circulator employed. For example, in a preferred embodiment, one additional circulator is used for each foot of cooling fluid that is to be circulated through an area of not more than about 24 inches wide by 48 inches deep.

Preferably, motors 130 can be controlled to maintain a constant, predetermined velocity of cooling fluid flow past the biological material to be preserved, while at the same time maintaining an even distribution of cooling fluid temperature within +/−0.5 degrees centigrade at all points within tank 110. The substantially constant predetermined velocity of cooling fluid circulating past the biological material provides a constant, measured removal of heat, which allows for the vitrification of the biological material during freezing. In one embodiment, cooling fluid properties such as viscosity, temperature, et cetera, are measured and processed, and control signals are sent to motors 130 to increase or decrease the rotational speed or torque of impellers 132 as needed. In other embodiments, motors 130 are constructed to maintain a given rotational velocity over a range of fluid conditions. In such a case, the torque or rotational speed of impellers 132 imparted by motors 130 are not externally controlled. Of note is the fact that no external pumps, shafts, or pulleys are needed to implement a preferred embodiment of the present invention. Motors 130, or other circulators 134, are immersed directly in cooling fluid 140. As a result, cooling fluid 140 not only freezes biological material placed in tank 110, but cooling fluid 140 also provides cooling for motors 130.

Heat exchanging coil 120 is preferably a "multi-path coil," which allows refrigerant to travel through multiple paths (i.e., three or more paths), in contrast to conventional refrigeration coils in which refrigerant is generally restricted to one or two continuous paths. In addition, the coil size is in direct relationship to the cross sectional area containing the measured amount of the cooling fluid 140. For example, in a preferred embodiment, tank 110 is one foot long, two feet deep, and four feet wide, and uses a heat exchanging coil 120 that is one foot by two feet. If the length of tank 110 is increased to twenty feet, then the length of heat exchanging coil 120 is also increased to twenty feet. As a result, heat exchanging coil 120 can be made approximately fifty percent of the size of a conventional coil required to handle the same heat load. Circulators 134 such as motors 130, circulate chilled cooling fluid 140 over biological material to be frozen, and then transport warmer cooling fluid to heat exchanging coil 120, which is submersed in cooling fluid 140. In at least one embodiment, heat exchanging coil 120 is connected to refrigeration unit 190, which removes the heat from heat exchanging coil 120 and the system.

In a preferred embodiment, refrigeration unit 190 is designed to match the load requirement of heat exchanging coil 120, so that heat is removed from the system in a balanced and efficient manner, resulting in the controlled, rapid freezing of a material. The efficiency of the refrigeration unit 190 is directly related to the method employed for controlling suction pressures by the efficient feeding or the heat exchange coil 120 and the efficient output of compressors used in refrigeration unit 190. This methodology requires very close tolerances to be maintained between the refrigerant and cooling fluid 140 temperatures, and between the condensing temperature and the ambient temperature. These temperature criteria, together with the design of the heat exchange coil 120, allow heat exchange coil 120 to be fed more efficiently, which in turn allows the compressor to be fed in a balanced and tightly controlled manner to achieve in excess of twenty five percent greater performance from the compressors than that which is accepted as the compressor manufacturer's standard rating.

Note that in the embodiment illustrated in FIG. 1, refrigeration unit 190 is an external, remotely located refrigeration system. However, in another embodiment (not illustrated), refrigeration unit 190 is incorporated into another section of tank 110. It will be appreciated that various configurations for refrigeration unit 190 may be more or less appropriate for certain configurations of cooling unit 100. For example, if tank 110 is extremely large, a separate refrigeration unit 190 may be desirable, while a portable embodiment may benefit from an integrated refrigeration unit 190. Such an integration is only made possible by the efficiencies achieved by implementing the principles as set forth herein, and particularly the use of a reduced-size heat exchanging coil.

By virtue of refrigeration unit 190 and heat exchanging coil 120, in a preferred embodiment, the cooling fluid is cooled to a temperature of between −20 degrees centigrade and −30 degrees centigrade, with a temperature differential throughout the cooling fluid of less than about +/−0.5 degrees centigrade. In other embodiments, the cooling fluid is cooled to temperatures outside the −20 degrees centigrade to −30 degrees centigrade range in order to control the rate at which a substance is to be frozen. Other embodiments control the circulation rate of the cooling fluid to achieve desired freezing rates. Alternatively, the volume of cooling fluid may be changed in order to facilitate a particular freezing rate. It will be appreciated that various combinations of cooling fluid circulation rate, cooling fluid volume, and cooling fluid temperature can be used to achieve desired freezing rates.

Referring now to FIG. 2, a cross sectional view of the chilling apparatus illustrated in FIG. 1 indicating implementation of cooling systems suitable for freezing relatively large quantities of biological material; an embodiment of cooling system 100 suitable for freezing relatively large quantities of biological material is discussed. Reference numerals in FIG. 2 that are like, similar, or identical to reference numerals in FIG. 1 indicate like, similar, or identical features. Tank 110 contains cooling fluid 140, into which rack 150 may be lowered. Rack 150 is movably coupled to rack support 210, such that rack 150 may be raised or lowered to facilitate the placement of substances into tank 110.

In use, biological material to be frozen is placed in trays 155 of rack 150. Preferably, trays 155 are constructed of wire, mesh, or otherwise, so that cooling fluid 140 may freely circulate over, under, and/or around items placed thereon. Preferably, once the cooling fluid is chilled to a desired temperature, rack support 210 lowers rack 150 into tank 110, in order to submerge trays 155 in cooling fluid 140. Lowering rack 150 may be accomplished manually or using various gear, chain, and/or pulley configurations known to those skilled in the art. Circulators 134 circulate cooling fluid 140 across substances placed in trays 155 to provide quick and controlled freezing. It will be appreciated that other arrangements for immersing biological material into tank 110 may be employed, and that use of an automatic lowering system is not necessarily preferred for use in all circumstances.

Figure 2A:
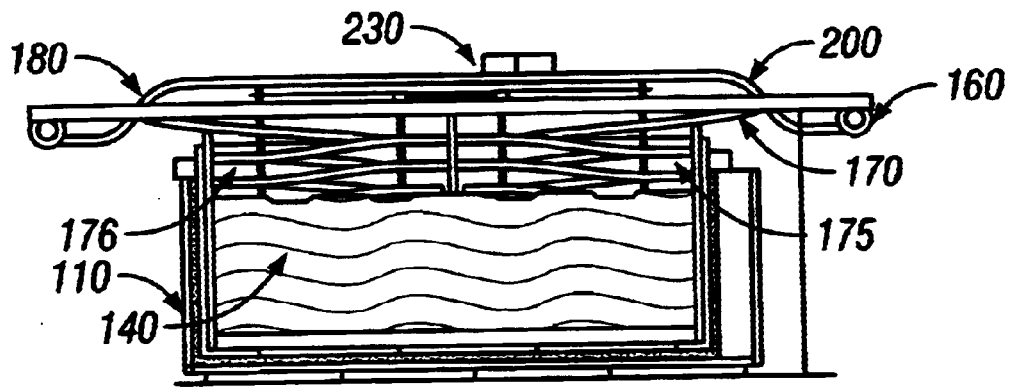
FIG. 2A is a cross sectional view of the chilling apparatus shown in FIG. 1, configured for use with a spiral conveyor according to one embodiment of the present invention.

Referring now to FIG. 2A, an embodiment of the present invention employing a multi-tiered spiral path conveyor system is discussed. As illustrated, spiral conveyor 200 may be configured to fit inside tank 110 in order to submerge biological material into cooling fluid 140. In use, once the cooling fluid is chilled to a desired temperature, materials to be frozen are fed into an input feed 160 where they are taken onto conveyor belt 170. The material travels from input feed 160, into the cooling fluid 140 on downward spiral 175, out of cooling fluid 140 on upward spiral 176, and out of spiral conveyor at output feed 180. As noted earlier, the cooling fluid 140 is preferably kept at a constant predetermined temperature, and circulated at a rate that ensures rapid, safe freezing of material to be frozen. The time the material spends submerged in cooling fluid 140 can be varied by adjusting the drive unit, 230, or by other suitable means. Ideally, the speed of conveyor belt 170, in combination with the temperature and circulation rate of cooling fluid 140, will be adjusted so that exactly the desired amount of heat will be removed from materials as they travel through tank 110 on the multi-tiered spiral path conveyor system 200.

Figure 3:
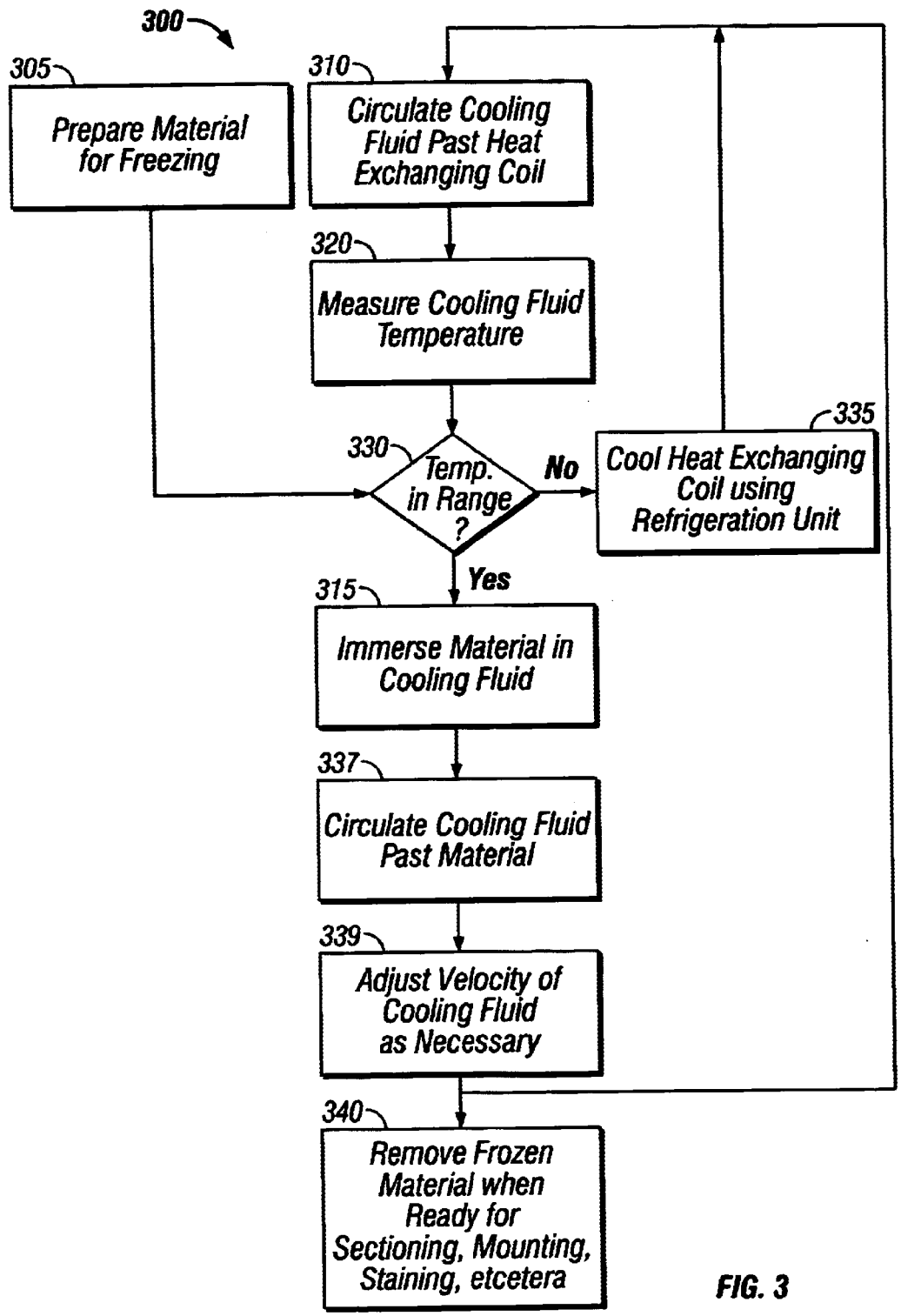
FIG. 3 is a flow diagram illustrating a system implemented according to at least one embodiment of the present invention.

Referring now to FIG. 3, a method according to one embodiment of the present invention is illustrated, and designated generally by reference numeral 300. The illustrated method begins at step 310, where cooling fluid is circulated past a heat exchange coil. The heat exchange coil is operably coupled to a refrigeration system as discussed above, and is used to reduce the temperature of the cooling fluid as the cooling fluid is circulated past the heat exchange coil. In step 320, the temperature of the cooling fluid is measured, and the method proceeds to step 330, where it is determined whether the temperature of the cooling fluid is within an optimal temperature range. This optimal cooling fluid temperature range may be different for different applications, however a preferred optimal temperature range for many applications is between −20 degrees centigrade and −30 degrees centigrade.

Should the cooling fluid temperature be determined not to be within an optimal, predetermined temperature range, step 335 is performed. In step 335, the heat exchanging coil is cooled by a refrigeration unit, and the method returns to step 310, in which the cooling fluid is circulated past the heat exchange coil in order to lower the temperature of the cooling fluid. Preferably, steps 310, 320, 330, and 335 are performed continually until the cooling fluid reaches the optimal temperature range.

The temperature of the cooling fluid used to freeze the biological material is an important element of at least one embodiment of the present invention. In order to achieve vitrification using conventional processes, biological material is generally quenched in liquid nitrogen, at a temperature of −196 degrees centigrade. Such a drastic change in temperature over a very short period of time freezes water within cell structures so quickly that ice crystals do not have a chance to form. However, freezing biological material by quenching in liquid nitrogen can cause stress fractures in cellular membranes, thereby limiting the usefulness of quenching in liquid nitrogen for cryopreservation. Since the temperatures used in a preferred embodiment of the present invention are between −20 degrees centigrade and −30 degrees centigrade, stress fractures due to temperature changes are minimized, and vitrification can be achieved with far less damage to cellular membranes.

While the cooling fluid is being cooled to the proper temperature, biological material to be frozen may be chemically prepared for freezing in step 305. It will be appreciated that materials to be used for pathology do not normally require chemical preparation, and foregoing step 305 by plunging materials to be frozen directly into a cooling fluid is consistent with the teachings set forth herein. As noted earlier, biological material includes, but is not limited to, viable single cells, tissues and organs, nucleic acids, and other biologically active molecules. The biological material does not have to be species specific. Chemically preparing the biological material may include pretreatment of the biological material with agents (stabilizers) that increase cellular viability by removing harmful substances secreted by the cells during growth or cell death. Useful stabilizers include those chemicals and chemical compounds, many of which are known to those skilled in the art, which sequester highly reactive and damaging molecules such as oxygen radicals.

Chemically preparing biological material may also include an acclimation step (not illustrated). During or at some time after pretreatment, the biological material to be preserved may be acclimated to a temperature which is reduced from culturing temperatures, but still above freezing. This may help prepare the biological material for the cryopreservation process by retarding cellular metabolism and reducing the shock of rapid temperature transition. Note well, however, than an acclimation step is not required in order to practice the present invention.

In a preferred embodiment, chemically preparing biological material for freezing includes loading the biological material with a cryoprotectant. Loading generally involves the equilibration of biological material in a solution of one or more cryoprotectants. Substances utilized during loading may be referred to as loading agents. Useful loading agents may include one or more dehydrating agents, permeating and non-permeating agents, and osmotic agents. Both permeating agents such as DMSO and ethylene glycol, and a combination of permeating and non-permeating osmotic agents such as fructose, sucrose or glucose, and sorbitol, mannitol, or glycerol can be used. It will be appreciated that other suitable cryoprotectants may be employed consistent with the objects of the present invention.

After the cooling fluid reaches a proper temperature, step 315 is performed, in which the chemically prepared biological material is immersed in cooling fluid. As noted earlier, the biological material may be held in a container, or placed directly into the cooling fluid. The method then proceeds to step 337, in which a circulator, such as a submersed motor/impeller assembly or pump, is used to circulate the cooling fluid at the velocity previously discussed, past the immersed biological material. As the cooling fluid passes by the biological material, heat is removed from the material, which is at a higher temperature than the temperature of the cooling fluid, and is transferred to be cooling fluid, which transports the heat away from the biological material to be frozen. According to at least one embodiment of the present invention, a substantially constant circulation of cooling fluid past the biological material to be frozen should be maintained in order to freeze the prepared biological material such that the prepared material is vitrified.

After the cooling fluid is circulated past the biological material to be frozen, step 339 is performed. Step 339 adjusts the velocity of the cooling fluid as necessary to account for changes in the cooling fluid viscosity, temperature, and the like. Preferably, the velocity of the cooling fluid is held constant by adjusting the force provided by one or more circulators. Once the biological material has reached the desired frozen state, it is removed as shown in step 340. After the material is removed from the cooling fluid in step 340 by means previously discussed, it may be sectioned and thawed for histological, ultrastructural, and immunohistochemistry examinations, such as fluorescent labeled antibody staining.

The steps illustrated in FIG. 3 are shown and discussed in a sequential order. However, the illustrated method is of a nature wherein some or all of the steps are continuously performed, and may be performed in a different order. For example, at least one embodiment of the present invention uses a single circulating motor to circulate the cooling fluid. In such an embodiment, cooling fluid is circulated past a heat exchanging coil as in step 310, and past the biological material to be preserved in step 337 at the same time. In addition, one embodiment of the present invention measures cooling fluid temperatures, viscosities, and other fluid properties continually, and at multiple locations within the system.

In yet another embodiment, some properties of the cooling fluid are not directly measured. Rather, the change in cooling fluid properties is determined indirectly from the rotational speed of a circulation motor. If the motor is turning at a slower rate, then additional power can be supplied to the motor to return the motor to the desired rotational speed, thereby compensating for the change in cooling fluid properties. In at least one embodiment, a motor is configured to maintain a substantially constant rate of rotation. This substantially constant rate of rotation will result in a substantially constant rate of cooling fluid circulation.

A test of one embodiment of the present invention was performed in which five milliliters (5 ml) of water was frozen in a graduated container. Upon freezing, there was less than one percent increase in total volume, much less than expected with conventional freezing. In another test, ice was frozen in sheets in a conventional freezer, and in a cooling system according to a preferred method of the present invention. After freezing, the ice was examined under dark microscope. As expected, the conventional ice displayed a crystalline pattern, whereas the ice frozen according to the principles of the present invention exhibited no light displacement, indicating little to no ice crystal formation.

Figure 4:
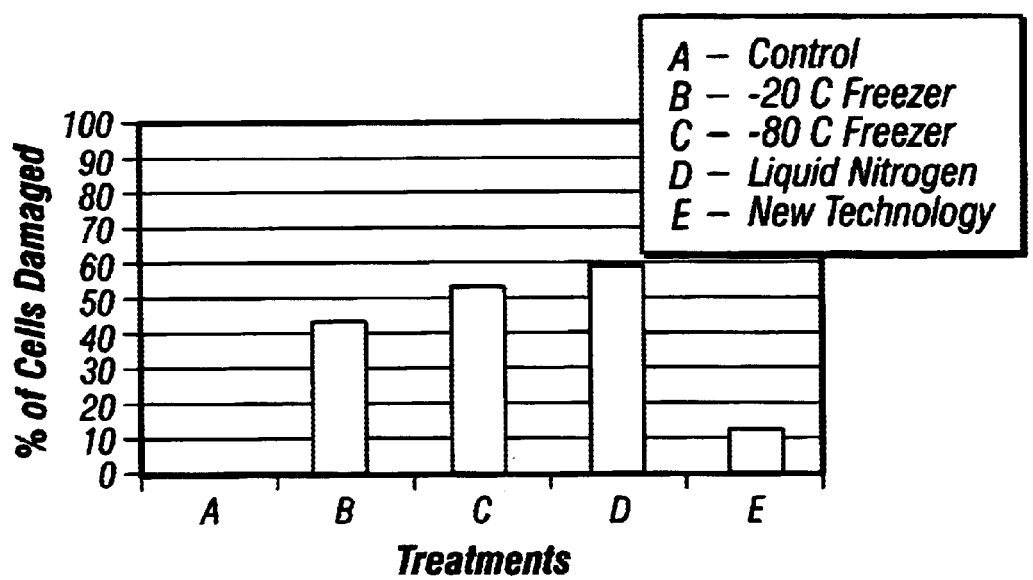
FIG. 4 is a bar chart showing the results of experimental comparisons between various prior art freezing methods and a freezing method according to a preferred embodiment of the present invention.

Refer now to FIG. 4, in which experimental results comparing various cryopreservation methods are compared. Bar graph 400 compares the number of individual cells damaged by use of four different cryopreservation methods B, C, D, and E against a control group A. No cryopreservation was performed on control group A, method B used a conventional freezer to freeze cells to a temperature of −20 degrees centigrade, method C used an ultralow freezer to freeze cells to a temperature of −80 degrees centigrade, method D used liquid nitrogen to freeze cells to a temperature of −196 degrees centigrade, and method E used a preferred embodiment of the present invention to freeze cells to a temperature of −25 degrees centigrade.

The results of the experiments, shown in bar graph 400, used plant tissue (seedless grapes) which were frozen by the conventional methods previously discussed, as well as by the method as embodied by the present invention, without any form of preparation or cryoprotectant. The frozen plant tissue was then thawed and thin sections were cut and examined, unstained, using phase-contrast microscopy. Plant tissue was employed in the experiments because gross distortion of the tissue by ice crystal formation or water expansion caused by freezing would disrupt the tissue's cell wall structure and could be readily observed. The results, as illustrated in FIG. 4, clearly show the superiority of the method performed according to a preferred embodiment of the present invention. As expected, the control, A, exhibited no cellular damage. Method B, the −20 C. freezer, exhibited damage in approximately 45% of the cellular wall structures; method C, the −80 C. freezer, exhibited damage in approximately 55% of the cellular wall structures; method D, liquid nitrogen, exhibited damage in approximately 59% of the cellular wall structures. However, the method performed according to a preferred embodiment of the present invention exhibited only about 12.5% cellular damage.

Figure 5A:
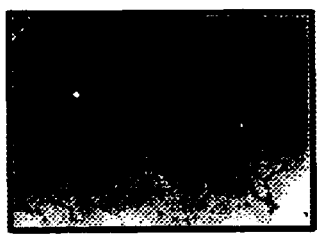
FIG. 5 illustrates views, as seen through a microscope, of the morphological appearance of noncryoprotected grape tissue following freeze-thaw cycles of the method of liquid nitrogen and the freezing method according to a preferred embodiment of the present invention.
Figure 5B:
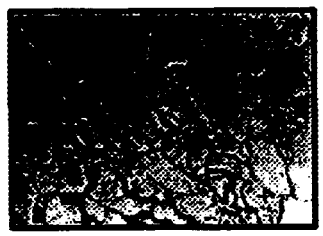
Figure 5C:

The superiority of the method performed according to a preferred embodiment is also seen in FIG. 5, which illustrates views, as seen through a phase-contrast microscope, of the morphological appearance of noncryoprotected grape tissue following freeze-thaw cycles of the method of liquid nitrogen and the freezing method according to a preferred embodiment of the present invention. Note in FIG. 5 the altered form and structure of the tissue indicating cellular wall damage is seen to be considerably less in the freeze-thaw method performed according to a preferred embodiment than that seen in the view of tissue freeze-thaw cycled with a method using liquid nitrogen.

Figure 6A:
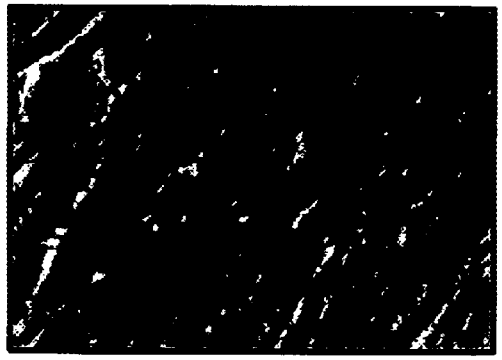
FIG. 6 illustrates views, as seen through a microscope, of the morphological appearance of heart tissue after freezing using standard cryopreparative techniques, and after application of the method according to a preferred embodiment of the present invention.
Figure 6B:
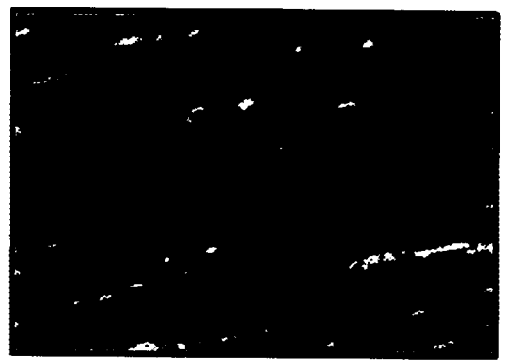

Referring now to FIG. 6, views, as seen through a microscope, of the morphological appearance of heart tissue after freezing using standard cryopreparative techniques, and after application of the method according to a preferred embodiment of the present invention is discussed. FIG. 6 illustrates the results of a different experiment which was performed on tissue samples collected post-mortem from mice and canine cadavers. Tissue samples were collected from five organ systems: ovarian, heart, liver, kidney, and lung. Tissues were prepared for conventional histology, cryo-sectioning, or ultrastructural examination using standard freezing techniques, and also following freezing by the method performed according to a preferred embodiment of the present invention. The resulting sections were then evaluated by a trained clinical pathologist. As expected, samples that were never frozen exhibited superior morphology upon histological evaluation. However, the pathologist report states that tissue frozen according to the method of a preferred embodiment of the present invention was at least as well preserved as tissue using standard cryogenic technology, and further that several types of tissue, most notably kidney and muscle (heart) demonstrated marked improvement in tissue integrity when frozen according to the method embodied by the present invention. FIG. 6 clearly indicates that the standard cryopreparative technique has numerous artifacts, such as "accordion folds" 605 seen within the heart muscle sample, as compared to the heart muscle sample which underwent the method as embodied by the present invention.

Figure 7A:
FIG. 7 is an electron microscope view illustrating the complex ultrastructural features such as cellular mitochondria that may be seen after application of the method according to a preferred embodiment of the present invention.
Figure 7B:

Refer now to FIG. 7, in which an electron microscope view illustrates the complex ultrastructural features, such as cellular mitochondria 705, seen after application of the method according to a preferred embodiment of the present invention as compared to a control which was never frozen. The electron microscope views illustrated in FIG. 7 clearly show little if any difference between the tissues frozen by the method according to a preferred embodiment of the present invention and control tissue which had never been frozen. Additionally, tissues frozen by the standard techniques of liquid nitrogen or mechanical freezing (not illustrated) exhibited significantly more damage upon examination than those of tissues frozen by the method according to a preferred embodiment of the present invention.

As stated earlier, a major problem with frozen sections created using the current technology is the loss of specific chemical reactions upon freezing. Loss of this activity renders these samples essentially useless for the more modern techniques of immunohistochemistry based upon antibody stain. An experiment which was conducted using a fluorescent labeled antibody (5.1H11, a human NCAM that is muscle specific) demonstrated that primary porcine satellite cells which were previously stained for fluorescence with this antibody continued to fluoresce after freezing when prepared according to the method of a preferred embodiment of the present invention. However, cells frozen in liquid nitrogen failed to fluoresce after thaw. The results of this experiment indicate that the method of a preferred embodiment will allow the newer techniques of cryopathology and immunohistochemistry to be applied in the areas of research and patient care.

Because the present invention can freeze biological material such that the material is vitrified, the formation of stress fractures in cellular membranes is minimized, and chemical activity within the cell is not lost after freezing, various embodiments of the present invention may find application in other medical fields with proper chemical preparation, such as skin grafts, cornea storage, circulatory vessel storage, freezing of transplant tissues, and infertility treatment, as well as in the investigation of molecular regeneration disease (cancer).

Although an embodiment of the present invention has been shown and described in detail herein, along with certain variants thereof, many other varied embodiments that incorporate the teachings of the invention may be easily constructed by those skilled in the art. Accordingly, the present invention is not intended to be limited to the specific form set forth herein, but on the contrary, it is intended to cover such alternatives, modifications, and equivalents, as can be reasonably included within the spirit and scope of the invention.

What is claimed is:

1. A method comprising:
    freezing a biochemically active tissue sample, wherein freezing includes:
        immersing the tissue sample in cooling fluid;
        circulating the cooling fluid past the tissue sample at a substantially constant predetermined velocity and temperature to freeze the tissue sample such that the tissue sample is vitrified; and wherein
            at least a portion of the tissue sample maintains its anatomical structure and
            remains biochemically active after thaw;
    thawing the tissue sample; and
    examining the thawed tissue sample.

2. The method as in claim 1, further comprising sectioning the tissue sample.

3. The method as in claim 1, wherein examining the thawed tissue sample includes histological examination.

4. The method as in claim 1, wherein examining the thawed tissue sample includes ultrastructural examination.

5. The method as in claim 1, wherein examining includes the use of immunohistochemistry examination.

6. The method as in claim 5, wherein immunohistochemistry includes fluorescent labeled antibody staining.

7. The method as in claim 1, wherein more than about 55 percent of the tissue sample exhibits no damage to cellular anatomical structure and remains biochemically active after thaw.

8. The method as in claim 1, wherein more than about 45 percent of the tissue sample exhibits no damage to cellular anatomical structure and remains biochemically active after thaw.

9. The method as in claim 1, wherein more than about 85 percent of the tissue sample maintains its anatomical structure and remains undamaged after thaw.

10. The method as in claim 1, wherein the cooling fluid is maintained at a temperature of between about −20 degrees centigrade and about −30 degrees centigrade.

11. The method as in claim 1, wherein the velocity of the cooling fluid past the tissue sample is about 35 liters per minute per foot of cooling fluid through an area not greater than about 24 inches wide and 48 inches deep.

12. The method as in claim 1, wherein, the cooling fluid is circulated by a motor/impeller assembly immersed in the cooling fluid.

13. The method as in claim 1, further comprising circulating the cooling fluid past a multi-path heat exchanging coil submersed in the cooling fluid, and wherein the heat exchanging coil is capable of removing at least the same amount of heat from the cooling fluid, as the cooling fluid removes from the tissue sample.

14. A method for use in preparing a tissue sample for examination, the method comprising:
    immersing a biologically active tissue sample in cooling fluid; and
    freezing the tissue sample directly to a temperature higher than about −30 degrees centigrade by circulating the cooling fluid past the tissue sample at a substantially constant predetermined velocity and temperature such that the tissue sample is vitrified, at least a portion of the tissue sample maintains its anatomical structure, and at least a portion of the tissue sample remains biochemically active after thaw.

15. The method as in claim 14, further comprising sectioning the tissue sample.

16. The method as in claim 14, further comprising thawing the tissue sample.

17. The method as in claim 14, wherein examination includes histological examination.

18. The method as in claim 14, wherein examination includes ultrastructural examination.

19. The method as in claim 14, wherein examination includes the use of immunohistochemistry examination.

20. The method as in claim 19, wherein immunohistochemistry includes fluorescent labeled antibody staining.

21. The method as in claim 14, wherein more than about 40 percent of the tissue sample maintains its anatomical structure and remains biochemically active after thaw.

22. The method as in claim 14, wherein more than about 80 percent of the tissue sample maintains its anatomical structure and remains biochemically active after thaw.

23. The method as in claim 14, wherein more than about 85 percent of the tissue sample maintains its anatomical structure and remains undamaged after thaw.

24. The method as in claim 14, wherein the cooling fluid is maintained at a temperature of between about −20 degrees centigrade and about −30 degrees centigrade.

25. The method as in claim 14, wherein the velocity of the cooling fluid past the tissue sample is about 35 liters per minute per foot of cooling fluid through an area not greater than about 24 inches wide and 48 inches deep.

26. The method as in claim 14, wherein, the cooling fluid is circulated by a motor/impeller assembly immersed in the cooling fluid.

27. The method as in claim 14, further comprising circulating the cooling fluid past a multi-path heat exchanging coil submersed in the cooling fluid, and wherein the heat exchanging coil is capable of removing at least the same amount of heat from the cooling fluid, as the cooling fluid removes from the tissue sample.

28. A system for use in preparing a tissue sample for examination, the system comprising:
    a cooling fluid reservoir configured to receive a biochemically active tissue sample for immersion in cooling fluid;
    one or more cooling fluid circulators configured to circulate said cooling fluid;
    a heat exchanging coil for removing heat from said cooling fluid;
    a refrigeration unit to remove heat from said heat exchanging coil; and wherein
        said cooling fluid reservoir, said one or more circulators, and said refrigeration unit cooperate to freeze the tissue sample directly to a temperature higher than about −30 degrees centigrade by circulating the cooling fluid past the tissue sample at a substantially constant predetermined velocity and temperature such that the tissue sample is vitrified, at least a portion of the tissue sample maintains its anatomical structure, and at least a portion of the tissue sample remains biochemically active after thaw.

29. The system as in claim 28, wherein examination includes histological examination.

30. The system as in claim 28, wherein examination includes ultrastructural examination.

31. The system as in claim 28, wherein examination includes the use of immunohistochemistry examination.

32. The system as in claim 31, wherein immunohistochemistry includes fluorescent labeled antibody staining.

33. The system as in claim 28, wherein more than about 40 percent of the tissue sample maintains its anatomical structure and remains biochemically active after thaw.

34. The system as in claim 28, wherein more than about 80 percent of the tissue sample maintains its anatomical structure and remains biochemically active after thaw.

35. The system as in claim 28, wherein more than about 85 percent of the tissue sample maintains its anatomical structure and remains undamaged.

36. The system as in claim 28, wherein the cooling fluid is maintained at a temperature of between about −20 degrees centigrade and about −30 degrees centigrade.

37. The system as in claim 28, wherein the velocity of the cooling fluid past the tissue sample is about 35 liters per minute per foot of cooling fluid through an area not greater than about 24 inches wide and 48 inches deep.

38. The system as in claim 28, wherein, the circulator is a motor/impeller assembly immersed in the cooling fluid.

39. The system as in claim 28, wherein the cooling fluid is circulated past a multi-path heat exchanging coil submersed in the cooling fluid, and wherein the heat exchanging coil is capable of removing at least the same amount of heat from the cooling fluid, as the cooling fluid removes from the tissue sample.

* * * * *